United States Patent

Chen et al.

[11] Patent Number: 5,138,052
[45] Date of Patent: Aug. 11, 1992

[54] L-683,590 MICROBIAL TRANSFORMATION PRODUCT

[75] Inventors: Shieh-Shung T. Chen, Morganville; Linda S. Wicker, Westfield; Byron H. Arison, Watchung, all of N.J.

[73] Assignee: Merck & Co., Inc., Rahway, N.J.

[21] Appl. No.: 666,466

[22] Filed: Mar. 5, 1991

Related U.S. Application Data

[63] Continuation of Ser. No. 544,802, Jun. 25, 1990, abandoned, which is a continuation of Ser. No. 366,096, Jun. 13, 1989, abandoned.

[51] Int. Cl.$^5$ .............. A61K 31/395; A61K 31/695; C07D 498/16; C07F 514/291
[52] U.S. Cl. ..................................... 540/456; 540/452
[58] Field of Search ................ 540/456, 452; 514/63, 514/183, 291, 411

[56] References Cited

U.S. PATENT DOCUMENTS

| | | | |
|---|---|---|---|
| 3,244,592 | 4/1966 | Arai | 540/456 |
| 4,894,366 | 1/1990 | Okuhara et al. | 540/452 |

FOREIGN PATENT DOCUMENTS

| | | | |
|---|---|---|---|
| 0184162 | 6/1986 | European Pat. Off. | 540/456 |
| 0323042 | 7/1989 | European Pat. Off. | 540/456 |

OTHER PUBLICATIONS

J. Antibiotics, A15, pp. 231-241 by Arai, et al., contains an infrared spectrum of ascomycin.

Primary Examiner—Robert T. Bond
Attorney, Agent, or Firm—Robert J. North; Charles M. Caruso; Salvatore C. Mitri

[57] ABSTRACT

Described is a new L-679,934 (FK-506) antagonist, L-686,292, a C-15, C-31 bisdemethylated, derivative of L-683,590, produced under fermentation conditions utilizing the microorganism, Actinoplanacete sp. (Merck Culture Collection MA 6559) ATCC No. 53771. The macrolide reverses the immunosuppressant action of L-679,934 (FK-506), and can be used diagnostically as a tool to determine the presence of FK-506 macrolide type immunosuppressants in natural product broths, distinguishing such immunosuppressants from other chemical families such as the cycloporins.

1 Claim, 2 Drawing Sheets

L-686,292

IMMUNOMYCIN

L-683,590 MICROBIAL TRANSFORMATION PRODUCT

This is a continuation of application Ser. No. 07/544,802, field Jun. 25, 1990 now abandoned, which is a continuation of application Ser. No. 07/366,096, filed Jun. 13, 1989 now abandoned.

BACKGROUND OF THE INVENTION

1. Field of the Invention

This invention relates to a new L-679,934 immunosuppressant antagonist, I.-686,292, and a fermentation process for its production utilizing the microorganism *Actinoplanacete sp.* (MA 6559), ATCC No. 3771. The process involves culturing the microorganism and L-683,590 under conditions which effects C-15, C-31 bisdemethylation of L-683,590.

2. Brief Description of Disclosures in the Art

In 1983, the US FDA licensed cyclosporin, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular is the closely related macrolide immunosuppressant FK-520, produced by S. hygroscopcus subsp. yakushimaensis.

U.S. Pat. No. 3,244,592 to T. Arai describes the culturing of *Streptomyces hygroscopicus var. ascomyceticus* to produce the antifungal "ascomycin".

There is, however, no description in the literature of the production of any L-679,934 antagonist which will substantially reverse the immunosuppressant effects of L-679,934, and be useful in situations requiring the determination of FK-506 macrolide type activity as opposed to other chemical families such as the cyclosporins.

SUMMARY OF THE INVENTION

It has been found that a new L-679,934 antagonist, L-686,292, can be obtained by the fermentation of the microorganism Actinoolanacete so. (MA 6559), ATCC No. 53771, in the presence of the macrolide immunosuppressant L-683,590, under submerged aerobic conditions in an aqueous carbohydrate medium, containing a nitrogen nutrient, said conditions being conducted at a pH of about 7 for a sufficient time to selectively C-15, C-31 bisdemethylate L-683,590, i.e., remove two methyl radicals from two different methoxyl groups. L-686,292 is a minor fermentation product found in the broth along with L-687,795, the C-13, C-15; C-31 trisdemethylated analog of L-683,590, disclosed in copending Ser. No. 348,243 (Case 17911), filed May 5, 1989, having the same assignee, and hereby incorporated by reference. Major components in the broth include L-683,756, a C-13, C-31 bisdemethylated ring rearranged derivative of L-683,590 as described in Ser. No. 297,630 (Case 17832), filed Jan. 13, 1989, having the same inventorship and assignee, and L-683,742, the monodemethylated analog of L-683,590, as described in Ser. No. 213,025 (Case 17767) filed Jun. 29, 1988, having the same assignee, and both hereby incorporated by reference for this particular purpose.

The resultant L-686,292 exhibits L-679,934 antagonist activity, i.e., reversal of inhibition of T-cell activation caused by L-679,934, as demonstrated by the calcium ionophore (ionomycin) plus phorbol myristate acetate (PMA) induced T-cell stimulation assay, also referred to herein as the "T-cell proliferation assay". The principle of this assay is to measure the proliferation of mouse T lymphocytes stimulated with the combination of ionomycin plus PMA. L-679,934 inhibits T-cell proliferation in this assay, as indicated by reduced tritiated thymidine uptake. This inhibition of T-cell proliferation can be reversed with a compound, e.g. L-686,292, that binds to the cytosolic binding protein or molecule which mediates inhibition by L-679,934. In this case, competitive binding to the target molecule by the antagonist L-686,292 does not mediate inhibition of T-cell proliferation. This newly discovered protein is disclosed in Ser. No. 300,659 (Case 17866) filed on Jan. 19, 1989, and hereby incorporated by reference for this particular purpose.

In accordance with this invention, there is provided an L-679,934 antagonist, identified as L-686,292, produced by culturing a strain of *Actinoplanacete sp.* together with L-683,590 under submerged aerobic fermentation conditions in an aqueous carbohydrate medium, containing a nitrogen nutrient, for a sufficient time to produce product L-686,292.

Figures 1, 1A:
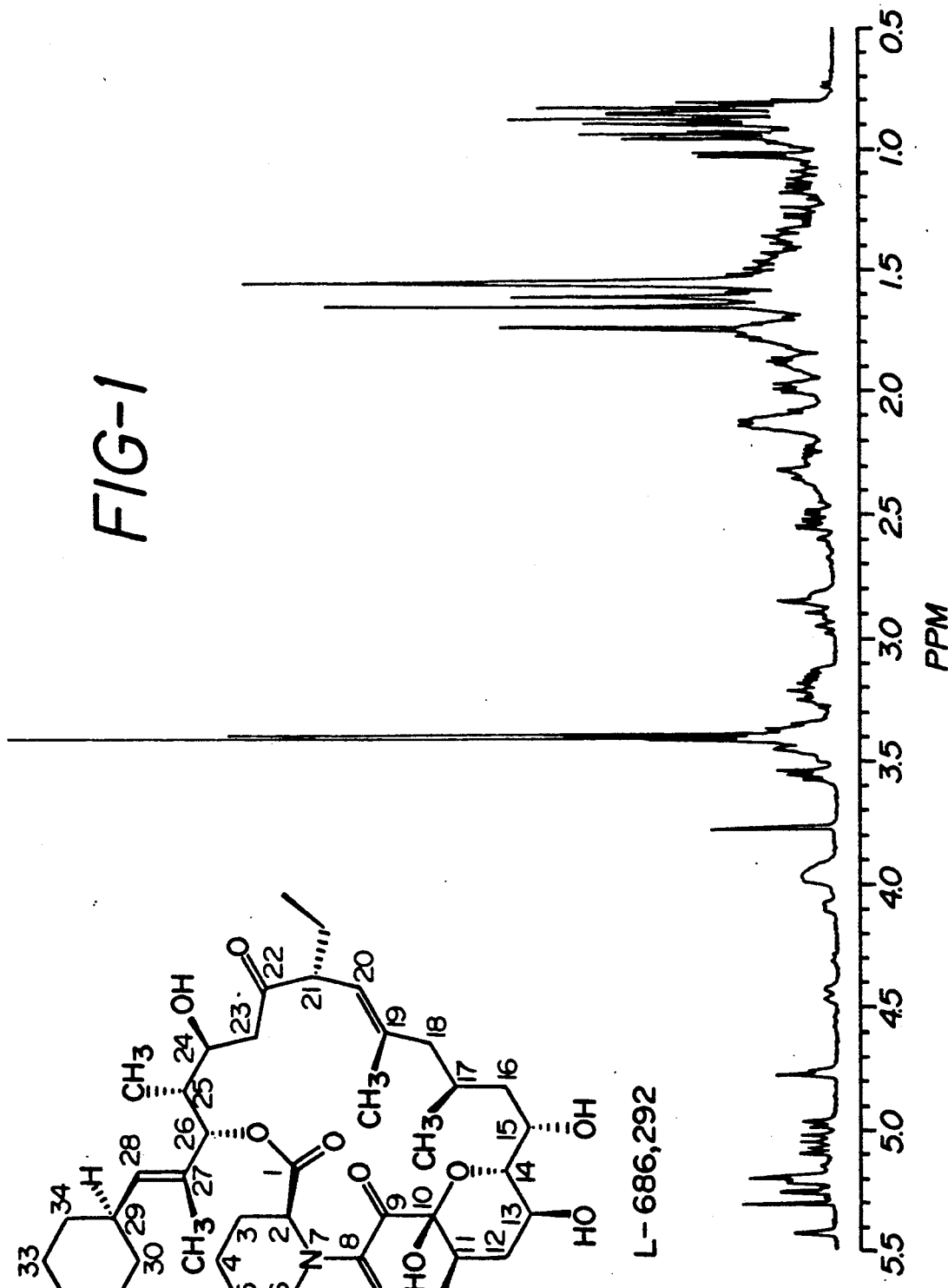
FIG. 1 is an $^1$H nuclear magnetic resonance (NMR) spectrum laken at 400 MHz to L-686,292 in CDCl$_3$ and illustrating the assigned molecular structure for L-686,292.
Figures 2, 2A:
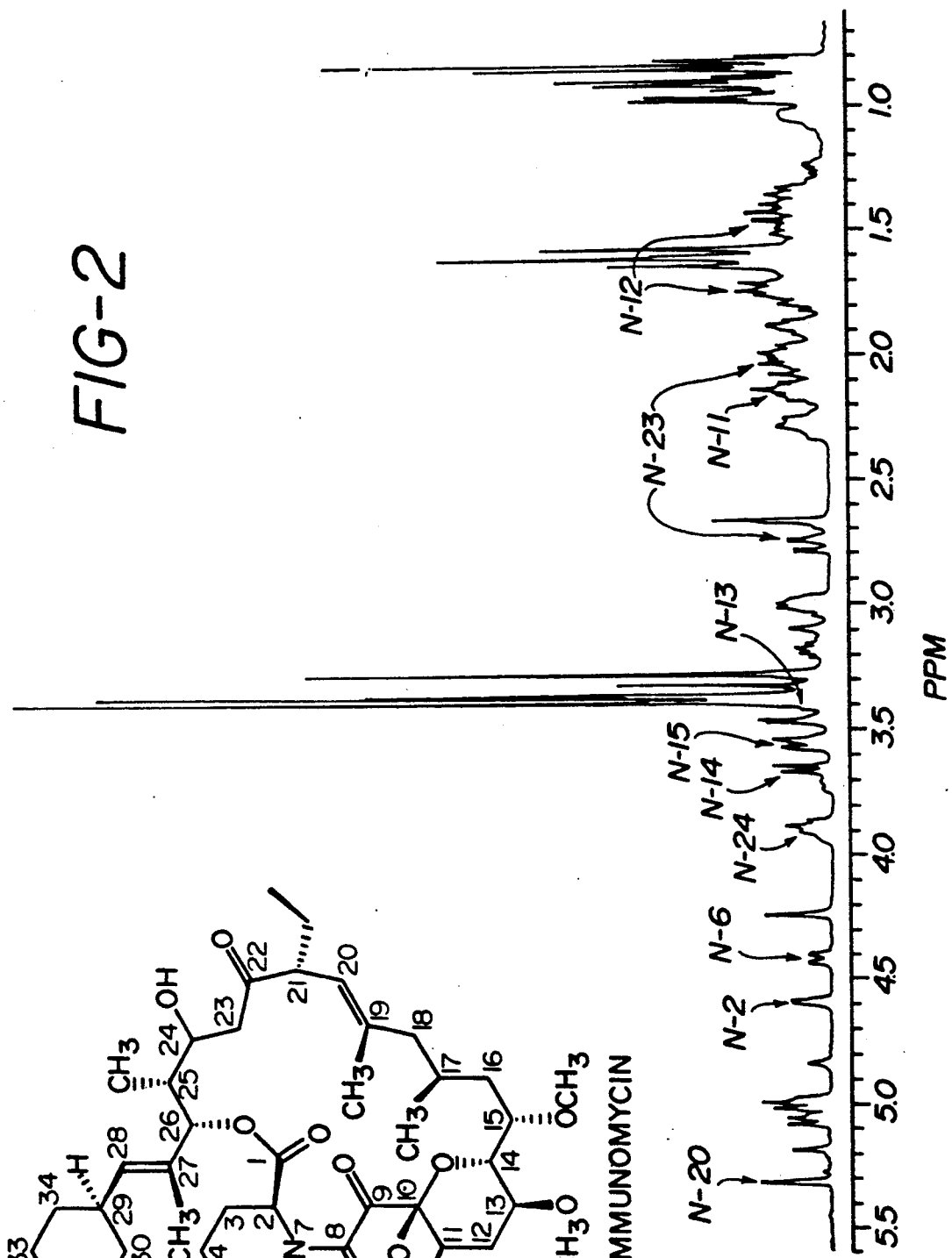
FIG. 2 is an $^1$H NMR spectrum taken at 400 MHz of L-683,590 (immunomycin) in CDCl$_3$.

The new antagonist, L-686,292, exhibits reversal of L-679,934 mediated inhibition of T-cell activation as measured in the T-cell proliferation assay, exhibits a proton nuclear magnetic resonance spectrum as identified in FIG. 1, and a molecular weight of 763 as determined by electron impact mass spectrometry.

DETAILED DESCRIPTION OF THE INVENTION AND PREFERRED EMBODIMENTS

The present invention involves the fermentation of *Actinoplanacete sp.* MA 6559, together with L-683,590 to produce L-686,292. The microorganism is currently on restricted deposit with the American Type Culture Collection, 12301 Parklawn Drive in Rockville, Md. as ATCC No. 53771, and in the Merck Culture Collection in Rahway, N.J. as MA 6559. The physical characteristics and taxonomy, including morphological, cultural, biological and physiological characteristics are briefly described hereinbelow.

On the basis of the taxonomic analysis performed thus far, the culture has tentatively been assigned in the order *Actinomycetales* and in the family *Actinoplanacea.* Further taxonomic characteristics are being examined to place this organism conclusively within a genus and species.

This culture grows well on routine media including trypticase soy agar (28° and 37° C.), yeast malt extract agar, glycerol asparagine agar, inorganic salt starch agar, oatmeal agar, Czapek Dox, Czapek solution agar and peptone agar, and Bennett's agar, all at 28° C.

Morphology—This culture grows as a branched filamentous mycelium with a diameter of 0.2–0.4 microns. Colonies are opaque, raised, and erose. Colony texture is rubbery on yeast malt extract agar but tends to be butyrous on other media where significant fragmentation of the mycelium is observed. The colony surface tends to be powdery in appearance. No diffusable pigments were observed.

Sporgangia—are predominantly spherical and range in size from 4–25 microns in diameter. Sporangia are generally visible by 21 days and tend to coalesce on glycerol asparagine agar. Spores are rod shaped with blunt ends (0.76×1.9 microns), non-motile and occur in long, unbranched chains of up to 150 microns in length.

Cultural characteristics of MA 6559 Yeast Extract-Malt Extract Agar (ISP Medium 2)

Vegetative mycelium is hyaline to yellow, aerial mycelium develops in 24–72 h and is buff to rose-pink and powdery in appearance. The reverse side is tan to reddish brown.

Oatmeal Agar (ISP Medium 3)

Vegetative mycelium is hyaline to yellow, the reverse side is hyaline to tan. Aerial growth is white to light rose-beige and powdery in appearance.

Inorganic Salts-Starch Agar (ISP Medium 4)

Light growth, scant aerial mycelium. Vegetative growth is hyaline and highly fragmented. Clearing of starch occurs at periphery of colonies noted by 7 d.

Glycerol Asparagine Agar (ISP Medium 5)

Vegetative growth is hyaline to yellow, the reverse side is hyaline to cinnamon brown. Aerial mycelium is powdery and white to rose-pink.

Peptide-Iron-Yeast Extract Agar (ISP Medium 6)

Vegetative growth is tan. No aerial growth observed, no melanoid pigments produced.

Tyrosine Agar (ISP Medium 7)

Vegetative growth is tan becoming deep purple as culture ages. Aerial mycelium is velvety to grayed rose-beige.

Czapek-Dox Agar

Vegetative growth is tan with a pink tone as the culture ages. Aerial mycelia are short and matted with a moist appearance.

The present invention process can be practiced with any "L-686,292-producing" strain of Actinoolanacete so.. and particularly preferred is the ATCC No. 53771 strain.

In general, L-686,292 can be produced by culturing (fermenting) the above-described "L-686,292-producing strain" in the presence of L-683,590 in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other veqetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

The L-683,590 starting material can be obtained by the fermentation of S. hygroscopicus var. ascomyceticus, ATCC No. 14891, as described in U.S. Pat. No. 3,244,592, and by the fermentation of S. hygroscopicus subsp. yakushimaensis No. 7278, (to produce FR-900520, or "FK-520", which is identical to L-683,590) as described in EPO Publication No. 0184162 to Fujisawa, said above references hereby incorporated by reference for this particular purpose.

As to the conditions for the production of L-686,292 in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of L-686,292. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of L-686,292 and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 10 hours to 24 hours, which may be varied according to fermentation conditions and scales. Preferably, the production cultures are incubated for about 24 hours at 27° C. on a rotary shaker operating a 220 rpm, wherein the pH of the fermentation medium is maintained at 7.0 to harvest.

Preferred culturing/production media for carrying out the fermentation include the following media:

|  | g/l |
|---|---|
| Seed Medium A | |
| Dextrose | 1.0 |
| Dextrin | 10.0 |
| Beef Extract | 3.0 |
| Ardamine PH | 5.0 |
| NZ Amine Type E | 5.0 |
| $MgSO_4.7H_2O$ | 0.05 |
| $K_2HPO_4$ | 0.37 |
| Adjust pH to 7.1 | |
| Add $CaCO_3$ 0.5 g/l | |
| Transformation Medium B | |
| Glucose | 10 |
| Hycase SF | 2 |
| Beef Extract | 1 |
| Corn Steep Liquor | 3 |
| Adjust PH to 7.0 | |

The produced L-686,292 can be recovered from the culture medium by conventional means which are commonly used for the recovery of other known biologically active substances. The L-686,292 substance produced is found int he cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product L-686,292 from the fermentation exhibits L-679,934 antagonist activity as indicated by the "T-cell proliferation assay" and possesses utility on this basis and exhibits the following physical characteristics:
1. White amorphous powder
2. Solubility in methanol
3. Molecular weight of 763, as determined by electron impact mass spectroscopy and is consistent with the assigned molecular structure in FIG. 1.

The L-686,292 obtained according to the fermentation processes as explained above can be isolated and purified in a conventional manner, for example, extraction, precipitation, fractional crystallization, recrystallization, chromatography, and the like.

Suitable formulations of the material may also include conventional pharmaceutically acceptable biolabile esters of L-686,292, formed via the hydroxy groups on the molecule, such as the acetate.

It is to be noted that in the aforementioned fermentation reactions and the post-treatment of the fermentation mixture therein, the tautomeric and conformational isomer(s) of L-686,292, including those due to rearrangement of the L-686,292 hemiketal ring system are also included within the scope of the present invention.

The L-686,292 of the present invention possesses L-679,934 antagonist activity and therefore is useful diagnostically as a tool to determine the presence of FK-506 macrolide type immunosuppressants in natural product broths, distinguishing such immunosuppressants from other chemical families such as the cyclosporins. Diagnostic devices utilizing this principle will be obvious to one skilled in the art.

The following examples are given for the purpose of illustrating the present invention and should not be construed as being limitations on the scope or spirit of the instant invention.

EXAMPLE 1

Microorganism and Culture Conditions

Frozen vegetative mycelium (MA 6559) ATCC No. 53771 was thawed and used to inoculate a 250 ml baffled shake flask containing 50 ml of autoclaved (sterilized) seed medium A consisting of (in units of grams/liter) dextrin 10.0, dextrose 1.0, beef extract 3.0, ardamine PH (Yeast Products, Inc.) 5.0, N-Z Amine type E 5.0, $MgSO_4.7H_2O$ 0.05, $KH_2PO_4$ 0.37, and $CaCO_3$ 0.5. The PH of the seed medium was adjusted to 7.1 before autoclaving. The seed was incubated in the seed medium at 27° C. for 24 hours on a rotary shaker operating at 220 rpm. A 2.5 ml aliquot of the resulting seed medium was used to inoculate a 250 ml non-baffled shake flask containing 50 ml of the following previously autoclaved (sterilized) transformation medium B. L-683,590 was added as a solution in dimethylsulfoxide to achieve a final concentration of 0.1 mg/ml concentration. The shake flask contents were subsequently incubated for 24 hours at 27° C. on a rotary shaker operating at 220 rpm.
1. Transformation medium B consisted of (in grams/liter) glucose 10.0; Hycase SF 2.0; beef extract 1.0; corn steep liquor 3.0; where the pH was adjusted to 7.0 before autoclaving.

Isolation and Purification Procedure for the Broth

The whole broth (500 ml) of transformation media B was extracted three times with methylene chloride (3×500 ml). Methylene chloride extracts were combined, dried over sodium sulfate, and concentrated under vacuum to an oily residue. The residue was dissolved in acetonitrile and subjected to high performance liquid chromatography (HPLC) purification.

HPLC was carried out on Whatman Partisil 10 ODS-3, 9.4 mm×25 cm column and monitored at 205 nm and 225 nm at 60° C. The column was developed at ml./min with linear gradient from 0.1% aqueous $H_3PO_4$-$CH_3CN$, 55:45 to 0.1% aqueous $H_3PO_4$-$CH_3CN$, 20:80 in 60 minutes. The compound was collected during repeated injections of the above described extract. The fractions at retention time 5 minutes were pooled, adjusted to pH 6.5 and evaporated to remove acetonitrile. The compound was further purified using a $C_{18}$ Sep-Pak (Waters Associates) and acetonitrile-water elution solvent to yield 1.2 mg. of product, designated as L-686,292.

Characterization

L-686,292 was characterized via NMR spectrometry yielding the proton NMR spectrum of FIG. 1, which confirms the assigned molecular structure.

EXAMPLE 2

T-Cell Proliferation Assay

1. Sample Preparation

Purified L-686,292, as prepared by HPLC above, was dissolved in absolute ethanol at 1 mg/ml.

2. Assay

Spleens from C57B1/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. Cultures containing ionomycin plus PMA were incubated with and without 1 ng/ml L-679,934 (FK-506) and various below-indicated dilutions of the sample (above-described purified L-686,292). L-686,292 was added in duplicate wells at 20 μl/well. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were 1 pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as percent inhibition of tritiated thymidine uptake (proliferation) as follows:

$$\% \text{ Inhibition} = 100 - \left[ \frac{\text{Mean cpm sample tested}}{\text{Mean cpm control medium}} \times 100 \right]$$

The results of % inhibition at various concentrations of L-686,292, in the presence and absence of 1 ng/ml L-679,934, are presented in the following table:

TABLE 1

Reversal of L-679,934 (FK-506)-Mediated Inhibition of T-Cell Proliferation by L-686,292

| | % Inhibition | |
|---|---|---|
| L-686,292 (ng/ml) | L-686,292 only | L-686,292 & L-679,934 (1 ng/ml) |
| 0 | 0 | 99 |
| 31 | 0 | 99 |
| 63 | 0 | 99 |
| 125 | 0 | 96 |
| 250 | 0 | 65 |
| 500 | 0 | 3 |
| 1000 | 0 | 0 |

Notes:
1. Mouse T cell cultures were pulsed with $^3$H-thymidine for 4 hours prior to harvesting at 48 hours.
2. Standard L-679,934 (1 ng/ml) gave 99% inhibition. The $IC_{50}$ for L-679,934-mediated inhibition was 0.32 ng/ml (0.4 nM).
3. $IC_{50}$ of reversal = 250 ng/ml = 328 nM, for L-686,292, and generally in the range of 100 to 400 $\times 10^{-9}$ molar.
4. Inhibition of proliferation by L-679,934 was reversed by the addition of 50 units/ml of recombinant human IL-2.

TABLE 2

L-686,292 Reverses Inhibition of T-cell Proliferation Mediated by L-679,934 but not by Cyclosporin A

| L-686,292 (ng/ml) | Inhibitor | % Inhibition |
|---|---|---|
| 0 | L-679,934 (1 ng/ml) | 97.1 |
| 1000 | L-679,934 (1 ng/ml) | 4.7 |
| 125 | L-679,934 (1 ng/ml) | 0 |
| 62.5 | L-679,934 (1 ng/ml) | 65.7 |
| 31.3 | L-679,934 (1 ng/ml) | 93.4 |
| 0 | Cyclosporin A (120 ng/ml) | 86.6 |
| 1000 | Cyclosporin A (120 ng/ml) | 95.6 |

Notes:
1. Inhibitors and L-686,292 were added at the initiation of culture. Cultures were pulsed with $^3$H-thymidine for 4 hours prior to harvesting at 48 hours.

Based on the data above, it is seen that L-b 686,292 can be used diagnostically as a tool to determine the presence of FK-506 macrolide type immunosuppressants in natural product broths, distinguishing such immunosuppressants from other chemical families such as the cyclosporins.

What is claimed is:

1. A compound which exhibits: a proton nuclear magnetic spectrogram and molecular structure as depicted in FIG. 1, and a molecular weight of 763 as determined by electron impact mass spectroscopy.

* * * * *